(12) United States Patent
Spolaczyk

(10) Patent No.: US 6,819,437 B2
(45) Date of Patent: Nov. 16, 2004

(54) APPARATUS FOR HANDLING LIQUIDS AND A PROCESS FOR OPERATING THE DEVICE

(75) Inventor: Reiner Spolaczyk, Hamburg (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 10/205,640

(22) Filed: Jul. 24, 2002

(65) Prior Publication Data

US 2003/0038950 A1 Feb. 27, 2003

(30) Foreign Application Priority Data

Aug. 24, 2001 (DE) .......................................... 101 41 544

(51) Int. Cl.[7] .............................................. G01B 11/14
(52) U.S. Cl. ....................... 356/624; 356/128; 250/577
(58) Field of Search ................................. 356/601, 609, 356/614, 622, 630, 128, 481–482, 504, 492–493, 624; 250/201.3, 577, 234–235, 559.4, 227, 461.2

(56) References Cited

U.S. PATENT DOCUMENTS

| | | | | |
|---|---|---|---|---|
| 3,768,910 A | * | 10/1973 | Zanoni | 356/614 |
| 3,847,485 A | * | 11/1974 | Zanoni | 356/614 |
| 4,246,489 A | * | 1/1981 | Yoshida et al. | 250/577 |
| 4,287,427 A | * | 9/1981 | Scifres | 250/577 |
| 4,582,809 A | * | 4/1986 | Block et al. | 250/227 |
| 4,699,516 A | * | 10/1987 | Bartz et al. | 356/445 |
| 4,804,268 A | * | 2/1989 | Mohnsen et al. | 356/338 |
| 4,945,245 A | * | 7/1990 | Levin | 250/461.2 |
| 5,305,071 A | * | 4/1994 | Wyatt | 356/73 |
| 5,594,242 A | * | 1/1997 | Konishi et al. | 356/614 |
| 5,633,708 A | * | 5/1997 | Svendsen | 356/128 |
| 5,737,084 A | * | 4/1998 | Ishihara | 356/614 |
| 5,877,856 A | * | 3/1999 | Fercher | 356/357 |
| 5,943,134 A | * | 8/1999 | Yamaguchi et al. | 356/357 |

FOREIGN PATENT DOCUMENTS

JP        58060222 A   *   4/1983   ........... G01F/23/28

* cited by examiner

Primary Examiner—Gregory J. Toatley, Jr.
Assistant Examiner—Sang H. Nguyen
(74) Attorney, Agent, or Firm—Sidley Austin Brown & Wood, LLP

(57) ABSTRACT

An apparatus for handling liquids and including a lighting installation for lighting an approximately punctiform illumination point in the room, an approximately punctiform light-receiving device having a photodetector for providing a measuring signal dependent on the intensity of the light received, an imaging system for imaging the illumination point onto the approximately punctiform light-receiving device, and an evaluation device for detecting the approaching of an interface between two media of different refractive indices to the illumination point by evaluating the measuring signals provided by the photodetector.

17 Claims, 4 Drawing Sheets

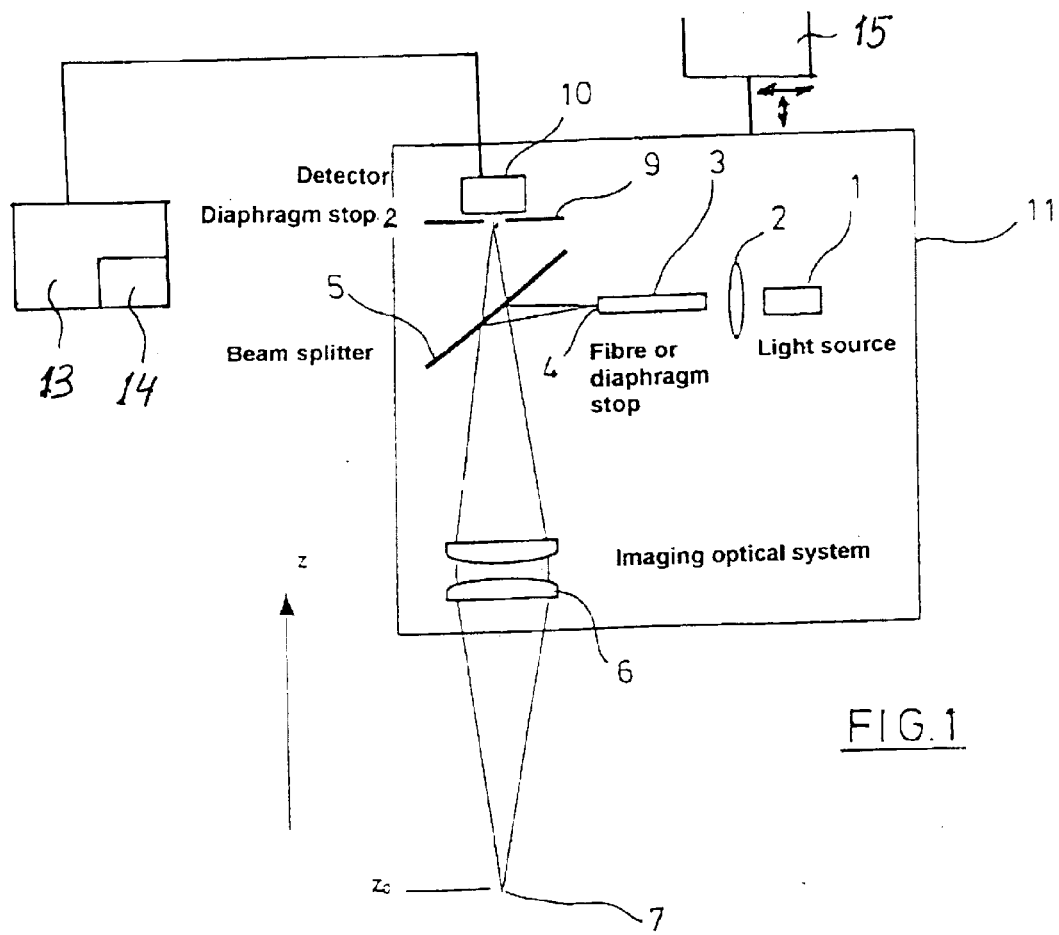
FIG.1
FIG.2
Dependence of diaphragm stop diameter
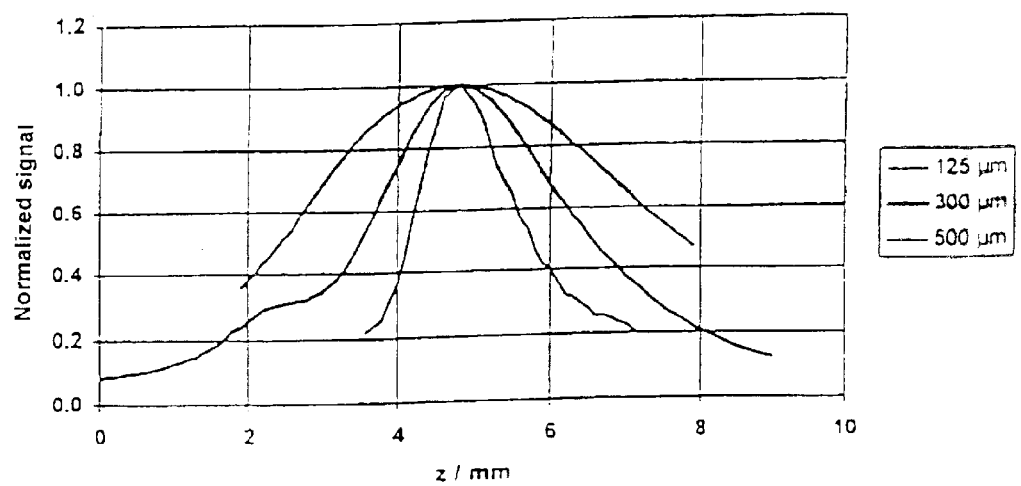

Bar code on an aluminium label

APPARATUS FOR HANDLING LIQUIDS AND A PROCESS FOR OPERATING THE DEVICE

BACKGROUND OF THE INVENTION

1. Field of the Invention

The invention relates to an apparatus for handling liquids and a process for operating the device.

2. Description of the Prior Art

An apparatus for handling liquids, in particular, can be an apparatus for proportioning and/or transporting and/or testing and/or processing liquids (e.g. chemically, physically or biologically). In the known apparatuses, operations are performed either manually or in a partially or completely automated manner. Thus, for example, manual pipettes, PC aided proportioning systems, and fully automatic proportioning stations are known for proportioning processes. Fully automatic handling stations (so-called "workstations") are available to proportion, test, and process liquids.

Both in manual and automatical pipetting, the reception of liquid requires that the pipette tip be dipped into the liquid, on one hand, but only up to an immersion depth as small as possible, on the other, because the error in proportioning increases with the depth of immersion and the vessel receiving the liquid could be damaged if the pipette tip was dipped to a large depth. If manual pipettes are employed the user has to ensure this by accurately checking the depth of pipette tip immersion. Supervising equipment is used if automatic proportioning devices are employed.

Thus, it been known already to use conductive pipette tips or particularly conductive sensors the approaching of which to the liquid is monitored by a capacity measurement or the dipping of which into the liquid is monitored by a resistance measurement. These solutions, however, are bound to conductive liquids or require that the sensors be at small distances from the liquids or be dipped into them. Conductive pipette tips involve relatively high expenses for the consumable material. Inserting specific level sensors into vessels in which the liquid is may be annoying while the samples are processed.

From WO 0042384 A1, a detection system for liquid levels has been known for use in automatic workstations. The system has a light source and a photodetector which are directed to the liquid and towards each other, at an angle. The light source produces a light beam which, when reflected from the liquid surface, can be detected by the photodetector. The signal outputted by the photodetector varies depending on the intensity of the reflected radiation which is incident thereon. This output signal, in turn, will vary when the photodetector (and the light source) nears the liquid surface in that it increases initially and decreases afterwards because the reflected light beam travels from one side to the other side of the photodetector.

The beam path of the optical system is introduced through the opening of a vessel in which the liquid is. The required angle between the incident beam and the emergent beam limits its use to vessels which are of a relatively large diameter or a relatively small depth. In vessels having a relatively small diameter or a relatively large depth, however, the beam path would be interrupted at the border of the opening so that a measurement would no longer be possible.

Accordingly, it is the object of the invention to provide an apparatus for handling samples which makes it more convenient to determine the location of the liquid level in vessels of a relatively small diameter and/or a large depth. It is a further object of the invention to provide a process for operating an inventive apparatus.

SUMMARY OF THE INVENTION

The object of the invention is achieved by an apparatus for handling liquids that has a lighting installation for illuminating an approximately punctiform illumination point in the room, an approximately punctiform light-receiving device having a photodetector for providing a measuring signal dependent on the intensity of the light received, an imaging system for imaging the illumination point onto the approximately punctiform light-receiving device, and an evaluation device for detecting the approach of an interface between two media of different refractive indices to the illumination point by evaluating the measuring signals provided by the photodetector.

In the inventive device, the approximately punctiform illumination point is imaged onto the approximately punctiform light-receiving device. As a result, the intensity of the light radiation received by the light-receiving device will vary and, hence, so will the measuring signal provided by the photodetector if an interface enters the illumination point between two media of different refractive indices. Thus, it can be ascertained whether or not there is an interface in the illumination point. This allows to establish the position of an interface which can be a liquid level, i.e. the interface between a liquid and air, for example. It further allows to establish the location of a surface of an object which can be non-covered, for example, or be covered by a medium transparent to the light of the lighting installation (e.g. a vessel bottom covered with a liquid).

To determine the position of an interface, it is possible to vary the relative position of the illumination point and the interface until the interface is in the illumination point. It further is possible to scan the surface of an object using the illumination point in order to judge on the position of the entire object and/or its identity on the basis of individual values or the course of the measuring signal.

Thus, the inventive apparatus specifically permits to determine the height of the liquid level in vessels (e.g. reaction vessels and in indentations of microtitration plates), the position and identity of vessels (e.g. reaction vessels and microtitration plates), and the position and identity of tools and aids (e.g. pipette tips in a rack). Since the light beam of the lighting installation and the imaging system are directed coaxially to the illumination point a non-contacting detection of interfaces is possible from a major distance and at a low lateral space requirement. This makes it easier to detect the liquid level in vessels having a relatively small opening and/or a relatively large depth.

To detect a liquid level free from trouble caused by adjacent vessel walls, it is possible to appropriately use light of a single wavelength to which a liquid (e.g. water) is opaque.

The interfaces detectable are both diffusely reflecting interfaces (e.g. dull surfaces) and substantially directionally reflecting interfaces (e.g. glossy surfaces or liquid surfaces). The measuring signal is particularly strong, above all, for substantially directionally reflecting interfaces if, according to an aspect, the surface normal line at the place where the interface is scanned by the illumination point is approximately coaxial to the illuminating light beam and the optical axis of the imaging system.

Preferably, the lighting installation comprises a light source of its own which can be a laser, LED or small bulb, for example.

The illumination point may be lighted by a linear light beam which can be produced by means of a laser, for example. On the linear light beam, the imaging system will then define a punctiform illumination point, which is imaged onto the approximately punctiform light-receiving device.

According to an aspect, the lighting installation also comprises an imaging system which images the light of a punctiform light source onto the illumination point. As a result, the illuminating light beam (or "light bundle") has its largest intensity in the illumination point. Along with imaging the illumination point onto the light-receiving device, this results in a measuring signal which is particularly strong.

According to an aspect, the light of the punctiform light source is fed to the imaging system via a beam splitter and the same imaging system images the illumination point onto the light-receiving device via the beam splitter. This realizes an incident-light measurement. Since there is only one imaging system the expenditure involved is relatively low.

According to an aspect, the lighting installation has a diaphragm stop and/or an optical waveguide in the optical path of the light source, the output of which is formed by the punctiform light source.

According to an aspect, the light beam lighting the illumination point has an aperture angle of 8° or less so that the light beam is adapted to be introduced into vessels of a relatively small opening diameter or a large depth without undergoing a fade-out in the external area.

According to an aspect, the distance of the illumination point from the imaging system is 100 mm or more, which enables a non-contacting measurement to be made for the liquid level in many ordinary vessels.

As a principle, the punctiform light-receiving device may be a photodetector having a particularly small light-sensitive area. According to an aspect, the punctiform light-receiving device has a diaphragm stop which determines the size of the receiving area.

According to an aspect, the evaluation device has means for filtering the measuring signal provided by the photodetector. This helps reduce a noise of the measuring signal and an impact of extraneous light.

According to an aspect, the apparatus is an automatic apparatus (e.g. a proportioning station or workstation) for handling liquids. Such an automatic station allows to control courses therein, e.g. the dipping of pipette tips into vessels, the processing of liquids in certain vessels, etc. because it detects the location and/or identity of liquids and/or objects.

According to an aspect, the apparatus has a shifting device to displace the relative position of the illumination point and the interface towards the optical axis of the imaging system and/or in a cross direction thereto.

The displacement of the relative position of the illumination point and the interface may be caused by the shifting device in various manners. According to an aspect, the relative position of the entire optical system formed by the lighting installation, the imaging system, and the light-receiving device and the interface is adapted to be displaced by means of the shifting device. This may be utilized for both a displacement towards the optical axis of the imaging system and a displacement transverse thereto. To this end, the entire optical system and/or the interface may be shifted to another place, e.g. by means of a specimen slide. According to an aspect, the shifting device has a zoom objective disposed in the imaging system for a displacement towards the optical axis. For a displacement transverse to the optical axis, the shifting device may have at least one scanning mirror in the imaging system.

According to another aspect, the shifting device is driven by a motor, e.g. for an integration into an automatic apparatus for handling liquids.

According to another aspect, the evaluation device controls the displacement of the relative position of the illumination point and interface by the shifting device. Then, displacement may be performed depending on the measuring signals, e.g. to adjust the illumination point to the interface and/or move it along the interface.

According to the inventive method for operating an inventive device,
  the distance between the illumination point and an interface is varied, the maximum of the measuring signal is determined while varying the distance, and the location of the illumination point is determined as the location of the liquid level at the maximum of the measuring signal, and/or
  the illumination point is displaced substantially in parallel with the interface, individual values or the course of the measuring signal are determined while the displacement is made, and the position and/or identity of the interface are determined while referring to the values or course of the measuring signal.

This method allows to determine the location of a liquid level and/or fixed object and/or the identity of a fixed object. An identification of the interface also identifies the liquid or object.

According to an aspect, the position and/or identity of the interface are determined by a comparison of the values measured to reference data on the configuration and/or the reflective characteristics of the interface. The reference data may be stored, for example.

Finally, according to an aspect, the illumination point is adjusted to a reference surface and the reference signal is measured that serves as a reference point for the measuring signal.

BRIEF DESCRIPTION OF THE DRAWINGS

The invention will be described in more detail below with reference to the accompanying drawings of an embodiment. In the drawings:

FIG. 1. shows a roughly schematic structure of an apparatus for detecting interfaces;

FIG. 2. shows how to measure a position on a water surface using different diaphragm stops in a graph with the water surface distance plotted on the abscissa, the measuring signal on the ordinate, and the diaphragm stop diameter as a curve parameter;

DETAILED DESCRIPTION OF THE PREFERRED EMBODIMENTS

Figure 3:
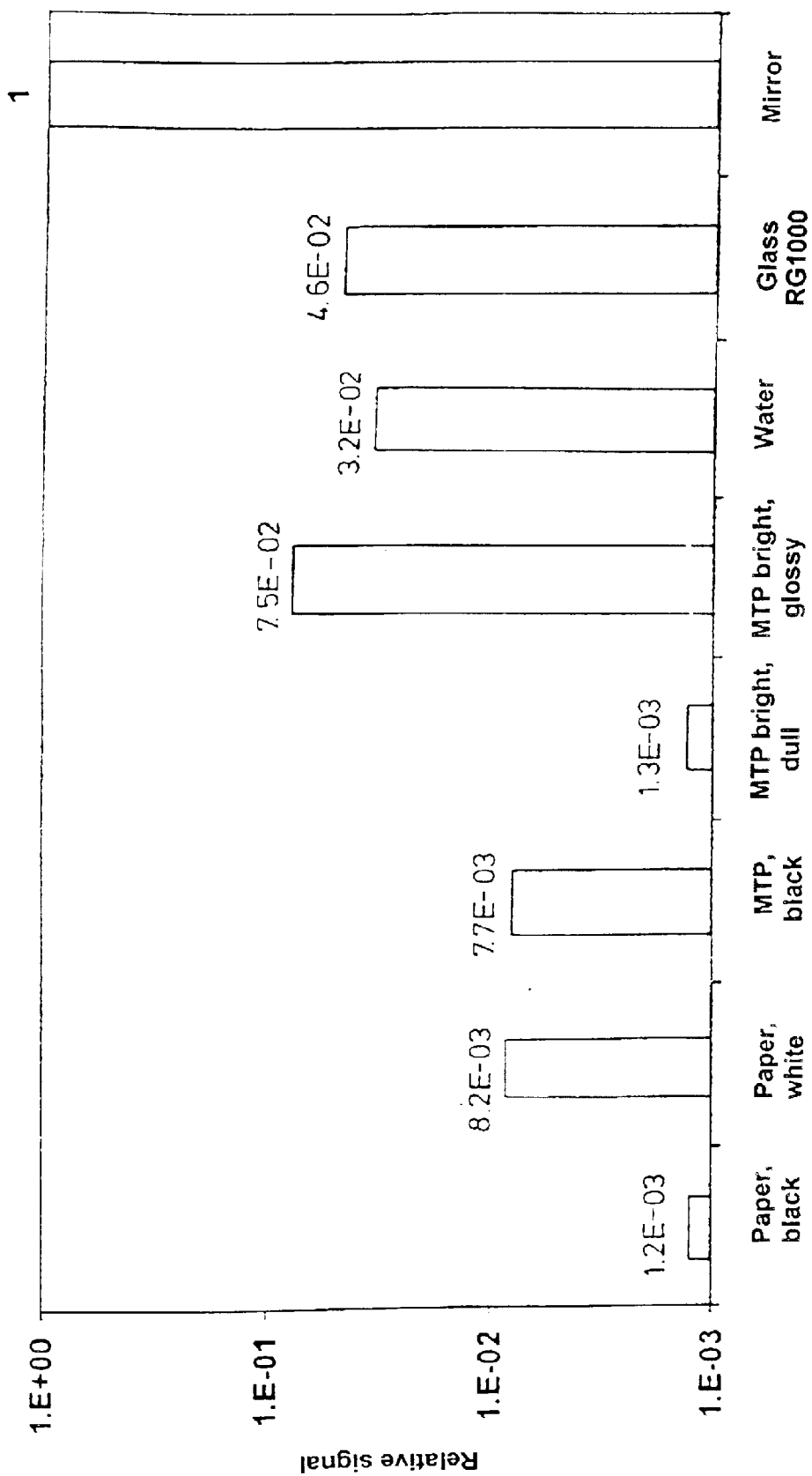
FIG. 3. shows the maximum signal of the light-receiving device when measuring reflections on various surfaces with the surface description plotted on the abscissa and the measuring signal on the ordinate.

Referring to FIG. 1, the apparatus has a light source 1 which directs a light beam onto a diaphragm stop 3 or optical waveguide through a lens 2.

Consequently, the aperture 4 of the diaphragm stop 3 or optical waveguide forms a punctiform light source from which the light is mirrored onto an imaging optical system 6. The imaging optical system 6 which comprises an objective lens focuses the light at a distance $z_0$. Hence, there is a punctiform illumination point 7 in the focus.

The imaging optical system 6 images the illumination point 7, via the beam splitter 5, onto the aperture 8 of a diaphragm stop 9 behind which a photodetector 10 is located. The aperture 8 of diaphragm stop 9 has the same diameter as has the aperture 4 of diaphragm stop 3. Moreover, the apertures 8, 4 are at the same optical distance from the beam splitter 5.

If a diffusely or directionally reflecting surface (with the direction of the latter being approximately perpendicular to the optical axis of the imaging optical system 6) at the illumination point reflected light passes through the diaphragm stop 9 on the photodetector 10. When the entire optical system 11 is moved in the z direction the light intensity measured by the photodetector 10 will change. It becomes a maximum when the reflecting interface 12 is exactly in the illumination point 7, i.e. at a distance $z_0$ from the imaging optical system 6. A measuring signal, which is provided by the photodetector 10, is evaluated by an evaluation device 13 which also includes means 14 for filtering the measuring signal.

Hence, the distance $z_0$ of an interface 12 or the position of the interface 12 is determined by scanning in a z direction. For changing a relative position of the interface 12 and the photodetector 10, there is provided a shifting device 15.

To detect a liquid surface, the light beam is led into a vessel through a vessel opening. If the overall aperture angle of the light beam is about 8° and the distance $z_0$ is 100 mm the clear diameter of the vessel opening has to be about 14 mm if measurement is to be made at a depth $z_0$ in the vessel.

While scanning is done in a direction transverse to the optical axis of the imaging optical system 6 (x direction) a change in intensity indicates an elevation or depression of the scanned area, but also a change in the degree of reflection.

The overall aperture angle of the light beam and the diameters of the openings 4, 8 of diaphragm stops 3, 9 act on the measuring accuracy of the apparatus. It will become the larger the larger the overall aperture angle is and the smaller the diameter is.

In an embodiment, the light source 1 is a laser diode having a wavelength of 670 manometers which is coupled via a light-transmitting fiber 125 μm in diameter. The diameter of aperture 6 of diaphragm stop 7 is abt. 100 μm. A Si photodiode VTB 5051 from EG & G FVCTEC serves as a photodetector.

FIG. 2 shows the increase in measuring accuracy with a decreasing diameter of the diaphragm stop opening while measuring the position of a water surface. The zero of z is chosen at random.

Since different interfaces reflect differently the height of the measuring signals covers a wide range. The above-described apparatus was used to measure the currents shown in FIG. 3 in the maximum of intensity on various interfaces on the photodetector. An object can be identified by means of the measuring signals which emanate from various interface contained therein.

Figure 4:
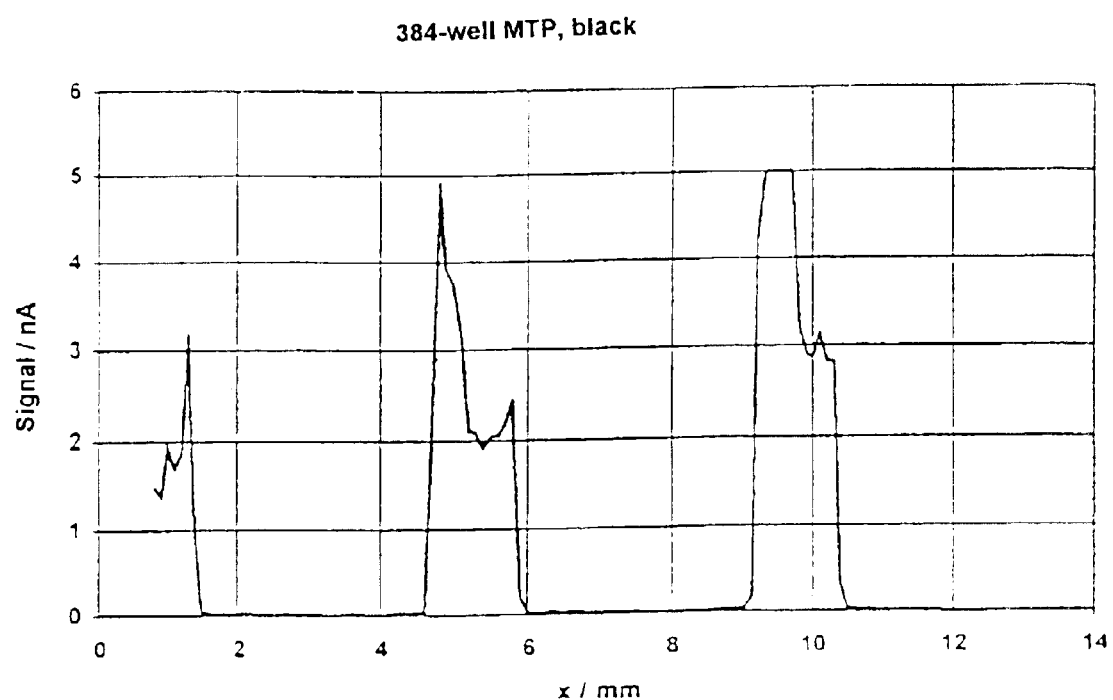
FIG. 4. shows a horizontal scanning of a 384-well microtitration plate in a graph with the scanning length plotted on the abscissa and the measuring signal on the ordinate.

In FIG. 4, the current measured on the photodetector 10 is shown scanning the surface of a black microtitration plate having 384 wells. The minima of the current indicate the scanning of a receptacle (a so-called "well") and the peaks there-between that of the surface portions between the receptacles. An evaluation of the measuring signal allows to ascertain that the characteristic dimensions of a 384-well microtitration plate are present. Thus, an automatic device can discover that there is a 384-well microtitration plate, and can accommodate proportionings thereto.

Figure 5:
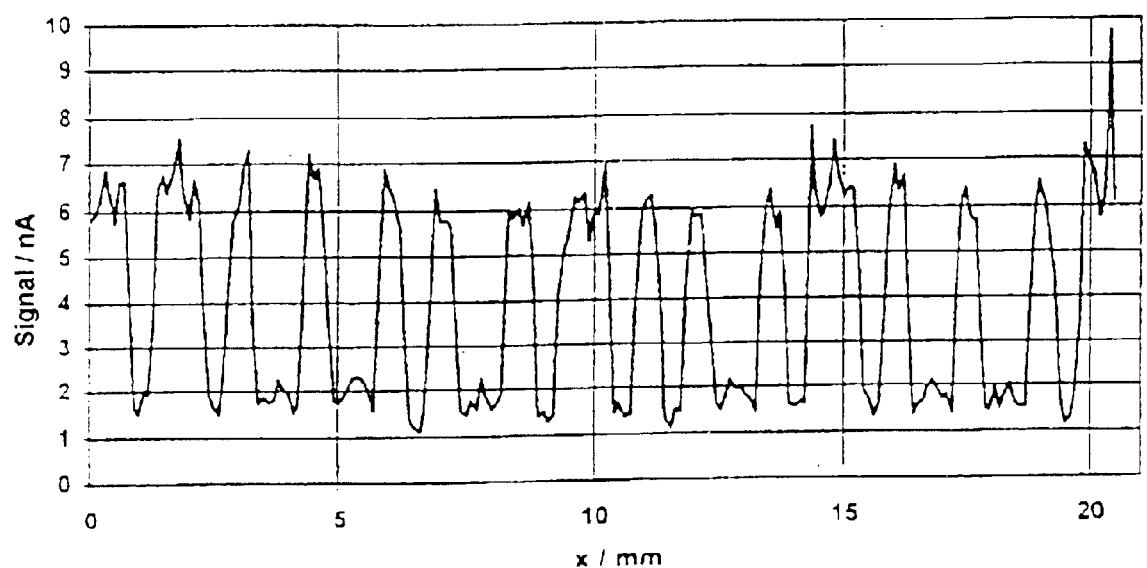
FIG. 5. shows the scanning signal of a bar code in a graph with the scanning length plotted on the abscissa and the measuring signal on the ordinate.
Figure 6:
FIG. 6. shows a bar code on an aluminum-coated label which relies on the scanning made in FIG. 5.

In FIG. 5, the current measured on the photodetector 10 is shown scanning the surface of the bar code which is shown in FIG. 6. The minima of intensity are associated with the dark stripes and the maxima of intensity are associated with the bright stripes of the bar code here. This enables an automatic identification of an object which is marked by bar codes.

What is claimed is:

1. A liquid handling apparatus for detecting at least one of liquid level, object, and identify of an object, the apparatus comprising:
    an installation for lighting an approximately punctiform illumination point in a room and including a system for imaging light of a punctiform light source on the illumination point at a distance from the imaging system;
    an approximately punctiform light-receiving device having a photodetector for providing a measuring signal dependent on intensity of a received light; the imaging system imaging the illumination point onto the approximately punctiform light-receiving device; and
    an evaluation device for detecting approaching of an interface between two media of different refractive indices to the illumination point by evaluating the measurement signal provided by the photodetector,
    wherein a light beam lighting the illumination point has an aperture angle of at most 8°.

2. The apparatus as claimed in claim 1, wherein a light beam lighting the photodetector and an optical axis of the imaging system are directed approximately coaxially to the photodetector.

3. The apparatus as claimed in claim 2, wherein the light beam and the optical axis of the imaging system are directed approximately coaxially to the interface.

4. The apparatus as claimed in claim 1, wherein the lighting installation comprises a light source which is one of a laser, LED, and a small bulb.

5. The apparatus as claimed in claim 1, wherein the light of the punctiform light source is fed to the imaging system via a beam splitter, and the imaging system images the illumination point onto the light-receiving device via the beam splitter.

6. The apparatus as claimed in claim 1, wherein the lighting installation has at least one of a diaphragm stop and an optical waveguide in an optical path of the light source.

7. The apparatus as claimed in claim 1, wherein a distance of the illumination point from the imaging system is at least 100 mm.

8. The apparatus as claimed in claim 1, wherein the punctiform light-receiving device has a diaphragm stop.

9. The apparatus as claimed in claim 1, wherein the evaluation device has means of filtering the measuring signal provided by the photodetector (10).

10. The apparatus as claimed in claim 1, further comprising a shifting device for changing a relative position of the photodetector and the interface towards at least one of the optical axis of the imaging system and perpendicular thereto.

11. The apparatus as claimed in claim 10, wherein the relative position of an optical system formed by the light source, the imaging system, the light-receiving device, and the interface is displaceable by the shifting device.

12. The apparatus as claimed in claim 11, wherein the shifting device is driven by a motor.

13. The apparatus as claimed in claim 12, wherein the evaluation device controls displacement of the relative position of the photodetector and the interface via the shifting device.

14. The apparatus as claimed in claim 13, wherein the apparatus detects at least one of location of liquid levels in at least one of reaction vessels and microtitration plates, location of the at least one of the reaction vessels and microtitration plates, pipette tips, identify of the at least one of the reaction vessels, microtitration plates, and pipette tips.

15. The apparatus as claimed in claim 13, wherein the apparatus detects objects having optically sensible markings in order to identify them.

16. The apparatus as claimed in claim 10, wherein the shifting device has a zoom objective in the imaging system.

17. The apparatus as claimed in claim 1 wherein the apparatus is an automatic apparatus.

* * * * *